(12) United States Patent
Doychinov et al.

(10) Patent No.: US 12,403,100 B2
(45) Date of Patent: Sep. 2, 2025

(54) NATURAL COMBINATION PRODUCTS AND METHODS FOR REGULATION OF TOTAL BLOOD CHOLESTEROL

(71) Applicant: Pure Care Pro LLC, Olympia, WA (US)

(72) Inventors: Plamen Doychinov Doychinov, Plovdiv (BG); Stoyan Doychinov Doychinov, Plovdiv (BG)

(73) Assignee: Pure Care Pro LLC, Olympia, WA (US)

( * ) Notice: Subject to any disclaimer, the term of this patent is extended or adjusted under 35 U.S.C. 154(b) by 1252 days.

(21) Appl. No.: 16/959,837

(22) PCT Filed: Jan. 4, 2019

(86) PCT No.: PCT/US2019/012382
§ 371 (c)(1),
(2) Date: Jul. 2, 2020

(87) PCT Pub. No.: WO2019/136274
PCT Pub. Date: Jul. 11, 2019

(65) Prior Publication Data
US 2021/0106541 A1    Apr. 15, 2021

Related U.S. Application Data

(60) Provisional application No. 62/613,714, filed on Jan. 4, 2018.

(51) Int. Cl.
| | | |
|---|---|---|
| A61K 31/045 | (2006.01) |
| A23L 33/105 | (2016.01) |
| A23L 33/145 | (2016.01) |
| A23L 33/24 | (2016.01) |
| A61K 36/06 | (2006.01) |
| A61K 36/87 | (2006.01) |
| A61K 36/899 | (2006.01) |

(52) U.S. Cl.
CPC .......... *A61K 31/045* (2013.01); *A23L 33/105* (2016.08); *A23L 33/145* (2016.08); *A23L 33/24* (2016.08); *A61K 36/06* (2013.01); *A61K 36/87* (2013.01); *A61K 36/899* (2013.01)

(58) Field of Classification Search
None
See application file for complete search history.

(56) References Cited

U.S. PATENT DOCUMENTS

| 3,294,637 A | 12/1966 | Cervelle |
|---|---|---|
| 2006/0020031 A1 | 1/2006 | Berlin |
| 2007/0166321 A1 | 7/2007 | Villeponteau |
| 2008/0292720 A1 | 11/2008 | Darlington, Jr. et al. |
| 2014/0314729 A1 | 10/2014 | Patel |

FOREIGN PATENT DOCUMENTS

| BG | 2003 U1 | 12/2014 | |
|---|---|---|---|
| CN | 1660732 A | 8/2005 | |
| CN | 101731599 A | 6/2010 | |
| CN | 102309004 A | 1/2012 | |
| CN | 103813722 A | 5/2014 | |
| CN | 104114040 A | 10/2014 | |
| CN | 104957602 A | 10/2015 | |
| CN | 107384969 A | 11/2017 | |
| GB | UK 1122650 | * 8/1968 | ............... A61K 3/86 |
| MX | 2013012781 A | 12/2013 | |
| WO | 2006/014790 A2 | 2/2006 | |
| WO | 2016/009403 A1 | 1/2016 | |

OTHER PUBLICATIONS

Chen et al., "Meta-Analysis of Natural Therapies for Hyperlipidemia: Plant Sterols and Stanols versus Policosanol," *Pharmacotherapy* 25(2):171-183, 2005.
Endo et al., "Biochemical aspect of HMG CoA reductase inhibitors," *Advances in Enzyme Regulation* 28:53-64, 1989.
Golomb et al., "Statin Adverse Effects: A Review of the Literature and Evidence for a Mitochondrial Mechanism," *Am. J. Cardiovasc. Drugs* 8(6):373-418, 2008.
Gouni-Berthold et al., "Policosanol: Clinical pharmacology and therapeutic significance of a new lipid-lowering agent," *American Heart Journal* 143(2):356-365, 2002.
Grundy et al, "Inhibition of 3-hydroxy-3-methylglutaryl-CoA reductase by mevinolin in familial hypercholesterolemia heterozygotes: Effects on cholesterol balance," *PNAS* 81:2538-2542, 1984.
Guardamagna et al., "The treatment of hypercholesterolemic children: Efficacy and safety of a combination of red yeast rice extract and policosanols," *Nutrition, Metabolism & Cardiovascular Diseases* 21:424-429, 2011.
Jing et al., "Comparison of the efficacy and safety of xuezhikang and lovastatin in hyperlipidemic patients with hypertension," *Journal of Clinical Epidemiology* 52:5S, 1999.
Kong et al., "The anti-inflammatory effect of kaempferol on early atherosclerosis in high cholesterol fed rabbits," *Lipids in Health and Disease* 12(115):1-12, 2013.
Marazzi et al., "Long-Term Effects of Nutraceuticals (Berberine, Red Yeast Rice, Policosanol) in Elderly Hypercholesterolemic Patients," *Advances in Therapy* 28(12):1105-1113, 2011.
Ngamukote et al., "Cholesterol-Lowering Activity of the Major Polyphenols in Grape Seed," *Molecules* 16:5054-5061, 2011.

(Continued)

*Primary Examiner* — Craig D Ricci
(74) *Attorney, Agent, or Firm* — Seed IP Law Group LLP

(57) ABSTRACT

This invention relates to compositions and methods relating a combination of naturally-occurring active ingredients, including active agents unrelated to statins, useful for the regulation total blood cholesterol. The inventive combination of active ingredients, including policosanol, mevinolic acid from dry yeast extract of red rice, dry extract of *Lespedeza captitata*, and dry grape seed extract, interrupts or inhibits the metabolic pathway leading to biosynthesis of cholesterol and cholesterol ester at multiple points and may also reduce high triglyceride levels. The present invention may be used to achieve normal blood serum LDL cholesterol concentrations and establish a healthy balance between LDL and HDL, all while significantly reducing the risk of statin-related side effects.

14 Claims, 5 Drawing Sheets

(56) References Cited

OTHER PUBLICATIONS

Qin et al., "Anthocyanin supplementation improves serum LDL- and HDL-cholesterol concentrations associated with the inhibition of cholesteryl ester transfer protein in dyslipidemic subjects," *Am. J. Clin. Nutr.* 90:485-492, 2009.
Reinoso et al., "Preclinical pharmacokinetics of statins," *Methods Find. Exp. Clin. Pharmacol.* 24(9):593-613, 2002.
Singh et al., "Policosanol Inhibits Cholesterol Synthesis in Hepatoma Cells by Activation of AMP-Kinase," *The Journal of Pharmacology and Experimental Therapeutics* 318(3):1020-1026, 2006.
Taylor et al., "Octacosanol in human health," *Nutrition* 19(2):192-195, 2003.
Loeper et al., "Action of the extract of '*Lespedeza Capitata*' on blood lipids," *Le Progres Medical* 4:79-80, Feb. 24, 1959. (5 pages) (with English Translation).
Yi et al., "Research progress on pharmacological effects of policosanol," *International Journal of Pathology and Clinical Medicine* 29(4):342-345, Aug. 2009. (9 pages) (with English Translation).
Extended European Search Report, dated Aug. 10, 2021, for European Patent Application No. 19735835.1-1112 / 3735296. (12 pages).
Examination Report, dated Mar. 16, 2022, for Indian Patent Application No. 202017033185. (9 pages).

\* cited by examiner

NATURAL COMBINATION PRODUCTS AND METHODS FOR REGULATION OF TOTAL BLOOD CHOLESTEROL

BACKGROUND

Technical Field

This invention relates to compositions and methods relating a combination of naturally-occurring active ingredients, including active agents unrelated to statins, useful for the regulation total blood cholesterol. The inventive combination of active ingredients, including policosanol, mevinolinic acid from dry yeast extract of red rice, dry extract of *Lespedeza capitata*, and dry grape seed extract, interrupts or inhibits the metabolic pathway leading to biosynthesis of cholesterol and cholesterol ester at multiple points and may also reduce high triglyceride levels. The present invention may be used to achieve normal blood serum LDL cholesterol concentrations and establish a healthy balance between LDL and HDL, all while significantly reducing the risk of statin-related side effects.

Description of the Related Art

About one third of coronary artery disease (ischemic heart disease) is due to the elevated levels of cholesterol and triglycerides.

The wide use of statins (inhibitors of 3-hydroxy-3-methyl-glutaryl coenzyme A-reductase) in the recent years has revolutionized the control of circulating blood lipids, a basic modifiable risk factor for atherosclerosis. The use of statins is known to lower cholesterol levels by inhibiting 3-hydroxy-3-methyl-glutaryl coenzyme A-reductase.

Studies show that statins are most effective in the treatment of cardiovascular diseases (CVD) as a secondary strategy for prevention, with contradictory use in those with high levels of cholesterol, but without preceding CVD. It is considered that their effect upon the overall mortality can be compared to the effect of antibiotics. However, patients taking statins may suffer an increased risk of undesirable side effects, including an increased risk of diabetes and abnormal liver enzyme tests, as well as rarer but severe side effects The first generation of statins (lovastatin, pravastatin, simvastatin) are actually derivatives of Aspergillus strains, while the later developed fluvastatin and atorvastatin are completely synthetic. All statins are not identical. They have different chemical structures that determine different pharmacokinetic properties Three statins (atorvastatin, simvastatin, fluvastatin) are lipophilic, which is the reason these are metabolized to hydrophilic compounds before their excretion by the kidneys. Atorvastatin, fluvastatin, pravastatin and rosuvastatin are administered in the form of active open hydroxy acids, while lovastatin and simvastatin are inactive lipophilic lactones, which after a person's oral intake are transformed in open hydroxy acids. Pravastatin and rosuvastatin are hydrophilic statins, which are redistributed in a lesser extent in the non-hepatic cells, for which reason they cause myopathy to a lesser degree.

The following Table 1 provides information on Lovastatin, Pravastatin, Simvastatin, Fluvastatin, and Atorvastatin.

TABLE 1

| | Lovastatin | Pravastatin | Simvastatin | Fluvastatin | Atorvastatin |
|---|---|---|---|---|---|
| Daily dose (mg) | 10-80 | 10-40 | 5-80 | 20-80 | 10-80 |
| Absorption (%) | 31 | 35 | 60-85 | 98 | 95-99 |
| Binding to Plasma proteins (%) | 95 | 40-50 | 98 | 99 | 98 |
| Renal excretion (%) | 30 | 60 | 13 | 6 | 2 |
| Plasma half-life (hr) | 2-4 | 0.9-1.6 | 1.3-2.4 | 1.2 | 14 |
| Lipo/hydrophilicity | Lipophilic | Hydrophilic | Lipophilic | Lipo- and hydrophilic- | Lipophilic |
| Passing through the blood-brain barrier | Yes | No | Yes | No | Yes |
| Metabolism by CYP450 | Yes | No | Yes | Yes | Yes |
| Trade name and form | Lipopres: tabl. 20, 40 mg | Lipostat: tabl. 10, 20 mg | Zocor: tabl. 10, 20, 40 mg | Lescol: 40, 80 mg | Sortis: 10, 20 mg |

The mechanism of action of the statins may be described as follows. In humans, about 40 various isoenzymes of cytochrome P (CYP) are present. Some of them are of great importance for the drug metabolism. All the statins (with the exception of pravastatin) pass through phase 1 metabolism by CYP 450. Atorvastatin, lovastatin and simvastatin are metabolized by CYP 3A4, fluvastatin and rosuvastatin are metabolized by CYP 2C9 and to a lesser extent by CYP 2C19.

Use of statins may result in unwanted side effects. Golumb et al., *Statin Adverse Effects: A Review of the Literature and Evidence for a Mitochondrial Mechanism, Am J Cardiovasc Drugs*, 8(6): 373-418 (2008) (Golumb). Further, a range of sources support a dose relation for statin adverse effects. Golumb, page 4. It is contemplated that use of the present invention might allow for a reduction in the use of conventional statins such that side effects will be significantly reduced or avoided. It is contemplated that use of the present invention may allow people on conventional statins to reduce their effective dosages.

This is because the inhibition of an isoenzyme responsible for the elimination of a certain statin leads to a significant increase of the drug's plasma concentration and increases significantly the risk for occurrence of side effects. The reverse is also true, that is, if the same isoenzyme is induced this will result in a lower plasma concentration of the statin and, respectively, to a reduction of its cholesterol lowering effect. Statin-related side effects may include: abnormalities in hepatic enzymes tests (ASAT, ALAT, GGT), as well as increase of bilirubin levels. These abnormalities may actually be severe adverse effects, and may especially include muscle damage. The most common statin-related adverse effects are the elevated hepatic enzymes and muscle problems. The present inventors have determined that in randomized clinical trials the reported adverse effects are relatively low, compared to their higher incidence when the trials are held in real world. In these randomized trials, the present inventors have determined that the statins increase the risk for unfavorable effect by 39%, compared to placebo.

Also, in the context of the side effects that can be observed during statin treatment it is important to know that statins are not to be given to patients with active hepatic disease or in cases of unexplainable lasting elevation of serum transaminases, cholestasis, myopathies, pregnancy, lactation, alcoholism, HIV-protease inhibitors, etc. The appearance of myalgia and elevated creatine phosphokinase also imposes discontinuation of the treatment. Statins should be prescribed very carefully in patients with rhabdomyolysis (destruction of the muscle tissue), renal impairment, or hypothyroidism. There is an increased risk for myopathy in concomitant intake of the following drugs: gemfibrozil and other fibrates, niacin (nicotine acid), cyclosporine, itraconazole, ketoconazole, erythromycin, clarithromycin, some medications for HIV, verapamil, the antidepressant nefazodone, etc.

Use of statins may also result in undesirable drug interactions. That is, if the isoenzyme is metabolizing more than one medication, a competitive process may be developed that reduces the metabolism of one or more of the substrates. Some of CYP 450 isoenzymes possess well-documented polymorphism, which means that in one part of the population accelerated metabolism is present and, in other part, metabolism is reduced. Often prescribed medications that suppress the CYP 3A4 function are macrolide antibiotics and azole antimycotics. Pravastatin and rosuvastatin are not metabolized by CYP 3A4 isoenzyme; therefore, they do not take part in interactions, based on this particular mechanism.

Lovastatin (mevinolin) is indicated for a broad clinical use in hypercholesterolemia (type 2A) and in hypercholesterolemia, accompanied by hypertriglyceridemia (type 2B). Lovastatin is a competitive inhibitor of 3-hydroxy-3-methylglutaril coenzyme A reductase. In the organism, lovastatin is hydrolyzed to an active metabolite, in particular β-hydroxy acid. When taken orally, it is eliminated 10% in the urine and 83% in excrement. A great part of lovastatin and its metabolites (>95%) are bound to plasma proteins. In the gastrointestinal tract, lovastatin is absorbed very slowly and incompletely, about 30% from the taken dose. Maximal concentration is reached in about 2 hours. After that a rapid drop follows, so after about 24 hours only 10% of the maximal concentration remains. It passes through the placental barrier, accumulates in the liver and is metabolized to β-hydroxy acid (mevinolinic acid), which actually blocks HMG-CoA reductase. Overt hypolipidemic effect comes after 2 weeks, and maximal hypolipidemic effect comes after 4-6 weeks.

Lovastatin is activated extremely slowly. When taken orally it is degraded in the stomach without the participation of any enzymes. Its lactone ring disintegrates and is transformed into mevinolinic acid, which in fact is the active metabolite and it inhibits directly HMG-CoA reductase. The residual lovastatin acts only when it is activated in the liver with the help of a local enzyme CYP 3A4, which is a part of the enzyme system of the total cytochrome P450. Thus three different hydroxy acids and lactone forms of lovastatin are originated or formed. This explains the slow and less effective action of lovastatin, which is effectively a prodrug that is metabolized into seven other structures, only some of which are able to work effectively.

There exists a need for products and methods to help achieve normal blood serum LDL cholesterol concentrations and to establish a healthy balance between LDL and HDL, all while significantly reducing the risk of statin-related side effects. The present invention satisfies this need in the form of products and methods that achieve greater efficiency and efficacy by combining multiple naturally-sourced components, including policosanol, mevinolic acid from dry yeast extract of red rice, dry extract of *Lespedeza capitata*, and dry grape seed extract, to introduce multiple points of interruption or inhibition of the metabolic pathway leading to biosynthesis of cholesterol and cholesterol ester. The present invention provides still further benefit in that it provides products and methods that also reduce high triglyceride levels.

BRIEF SUMMARY

This invention provides improved compositions and methods for regulating the level of total blood cholesterol for subjects in need thereof. The present invention may provide greater effectiveness in achieving one or more of normal blood serum LDL cholesterol concentrations, establishing a healthy balance between LDL and HDL, reducing high triglyceride levels, and significantly reducing the risk of statin-related side effects.

The present invention achieves the many benefits noted herein by providing a multi-pronged interruption or inhibition of the metabolic pathway leading to cholesterol and cholesterol esters biosynthesis. In a specific embodiment, the present invention includes products and methods of using products comprising natural ingredients, such as policosanol, mevinolic acid from dry yeast extract of red rice, dry extract of *Lespedeza captitata*, and dry grape seed extract, to form compositions useful for the reduction of effective doses of HMG-CoA reductase inhibitors that lower cholesterol levels, i.e., statins. Additionally, the compositions and methods of the present invention allow cholesterol levels to be controlled by other mechanisms not exploited by statins, e.g., inhibiting pancreatic cholesterol and reducing the solubility of cholesterol in the mycelia.

The inventive compositions and methods for modifying, controlling, or regulating the total blood cholesterol level comprise a composition that includes the following ratio of components:

policosanol from 1% to 5% (w/w);
dry extract of red rice yeast from 35% to 55% (w/w);
dry grape seed extract from 15% to 25% (w/w); and
dry extract of *Lespedeza capitata* from 25% to 40% (w/w).

In a preferred formulation, a capsule dosage form is provided that includes, per capsule, about 10 mg policosanol, about 700 mg dry extract of red rice yeast, about 240 mg dry extract of *Lespedeza capitata*, and about 120 mg dry grape seed extract.

In another preferred formulation, a capsule dosage form is provided that includes, per capsule, about 10 mg policosanol, about 330 mg dry extract of red rice yeast, about 240 mg dry extract of *Lespedeza capitata*, and about 120 mg dry grape seed extract.

The capsule may include, for example, hydroxypropylmethylcellulose (also known as HPMC or hypromellose), pullulan, gelatin, starch from cassava root or other vegetable sources, or cellulose.

In an alternative formulation, a tablet dosage form is provided that includes, per tablet, about 10 mg policosanol, about 700 mg dry extract of red rice yeast, about 240 mg dry extract of *Lespedeza capitata*, and about 120 mg dry grape seed extract.

In another alternative formulation, a tablet dosage form is provided that includes, per tablet, about 10 mg policosanol, about 330 mg dry extract of red rice yeast, about 240 mg dry extract of *Lespedeza capitata*, and about 120 mg dry grape seed extract.

Additional ingredients, or excipients, may include, for example, microcrystalline cellulose, polyvinylpyrrolidone, magnesium stearate, talc, film coating, e.g., polyvinyl alcohol, titanium dioxide color, polyethylene glycol, talc, etc. For example, microcrystalline cellulose may be added in an amount of 80 mg, polyvinylpyrrolidone may be added in an amount of 150 mg, magnesium stearate may be added in an amount of 10 mg, talc may be added in an amount of 10 mg, and film coating may be added in an amount of 40 mg.

Products of the present invention may comprise different forms including, for example, capsules, tablets, powders, liquids, etc.

Here, a preferred embodiment relates to capsules, because capsule formulations comprise minimal additional ingredients while providing moisture resistance and overcoming unpleasant tastes and odors. Capsule formulations are also easy to swallow and leave no trace of the capsule contents in the throat and trachea.

An alternative embodiment relates to tablets, and preferably film-coated tablets, because coating provides moisture protection and helps to overcome unpleasant tastes and odors. The tablets are made to be swallowed very easily and to leave no trace in the throat and trachea.

The following Table 2 provides a listing of active substances, relative content per dosage form, and proposed total content of a proposed daily intake regimen. It is noted that, while formulations may vary, a preferred embodiment of the present invention is presented in the table below. It is also noted that while the table below presents exemplary quantities for specific components of certain active ingredients, such as the amount of mevinolinic acid present in dry yeast extract of red rice, these amounts may vary depending on the source and preparation of the active ingredients.

In one embodiment, it is contemplated that formulations permitting some deviation in the amounts, or relative amounts, of the four active ingredients noted below will also serve the objectives of the present invention. Nonetheless, formulations providing variation from the stated amounts that are still within 5% (w/w) to 10% (w/w) of the stated amounts are most preferred. That is, potential formulation variations may include, for example, policosanol in amounts ranging from about 9-11 mg (w/w), dry yeast extract of red rice in amounts ranging from about 630-770 mg (w/w), dry extract of *Lespedeza capitata* in amounts ranging from about 216-264 mg (w/w), and dry extract of grape seed in amounts ranging from about 108-132 mg (w/w).

In another embodiment, it is contemplated that formulations permitting some deviation in the amounts, or relative amounts, of the four active ingredients noted below will also serve the objectives of the present invention. Nonetheless, formulations providing variation from the stated amounts that are still within 5% (w/w) to 10% (w/w) of the stated amounts are most preferred. That is, potential formulation variations may include, for example, policosanol in amounts ranging from about 9-11 mg (w/w), dry yeast extract of red rice in amounts ranging from about 290-365 mg (w/w), dry extract of *Lespedeza capitata* in amounts ranging from about 216-264 mg (w/w), and dry extract of grape seed in amounts ranging from about 108-132 mg (w/w).

TABLE 2

| ACTIVE SUBSTANCES | CONTENT IN 1 (one) tablet | CONTENT IN DAILY INTAKE (2 tablets in the evening, after meal) |
|---|---|---|
| Policosanol (total alcohols ≥95%) | 10 mg | 20 mg |
| Octacosanol | ≥50% | |
| Dry yeast extract of red rice | 700 mg | 1400 mg |
| Mevinolinic acid | 3.5 to 4.5 mg | 7 to 9 mg |
| Lovastatin | according to FDA, normal fermented red yeast rice contains 0.2% | |
| Dry Extract Lespedeza capitata | 240 mg | 480 mg |
| Kaempferol 3,7-dirhamnoside | standardized herbal extract | |
| Quercetin | | |
| Dry grape seed extract (proanthocyanidins ≥95%) | 120 mg | 240 mg |
| Catechin | standardized herbal extract | |
| Epicatechin | | |
| Gallic acid | | |
| Policosanol (total alcohols ≥95%) | 10 mg | 20 mg |
| Octacosanol | ≥50% | |
| Dry yeast extract of red rice | 330 mg | 660 mg |
| Mevinolinic acid | 1.5 to 2.2 mg | 3 to 4.5 mg |
| Lovastatin | according to FDA, normal fermented red yeast rice contains 0.2% | |
| Dry Extract Lespedeza capitata | 240 mg | 480 mg |
| Kaempferol 3,7-dirhamnoside | standardized herbal extract | |
| Quercetin | | |
| Dry grape seed extract (proanthocyanidins ≥95%) | 120 mg | 240 mg |
| Catechin | standardized herbal extract | |
| Epicatechin | | |
| Gallic acid | | |

Each of policosanol, dry extract of red rice yeast, dry extract of *Lespedeza capitata*, and dry extract of dry grape seed extract has been separately shown to reduce cholesterol. The present invention provides, for the first time, the combination of these four active components that, in turn, trigger four different mechanisms of action to interrupt or inhibit the biosynthesis of cholesterol and cholesterol esters. These four ingredients increase the effectiveness of the present invention by triggering a biochemical cascade mechanism of action. Each component individually has an effect on cholesterol reduction but together they affect several different stages of cholesterol metabolism and, thus, significantly increase the effectiveness of the compositions of the present invention. The presence of policosanol may increase the effectiveness of mevinolinic acid because both substances affect the same process of endogenous cholesterol synthesis. See, e.g., Singh et al., *Policosanol Inhibits Cholesterol Synthesis in Hepatoma Cells by Activation of AMP-Kinase*, PHARMACEUTICAL SCIENCES, COLLEGE OF PHARMACY, UNIVERSITY OF KENTUCKY, LEXINGTON, KENTUCKY May 18, 2006 and Endo et al., *Biochemical aspect of HMG CoA reductase inhibitors*, DEPARTMENT OF AGRICULTURAL AND BIOLOGICAL CHEMISTRY, TOKYO NOKO UNIVERSITY, FUCHU, TOKYO, JAPAN (1989).

Octacosanol triacontanol in policosanol decreases HMG-CoA reductase activity by reversible phosphorylation of several protein kinases, including AMP-activated kinase. The inventors note, however, that policosanol does not directly inhibit HMG-CoA reductase. See, e.g., Singh et al., *Policosanol Inhibits Cholesterol Synthesis in Hepatoma Cells by Activation of AMP-Kinase*, PHARMACEUTICAL SCIENCES, COLLEGE OF PHARMACY, UNIVERSITY OF KENTUCKY, LEXINGTON, KENTUCKY May 18, 2006.

Mevinolinic acid in the dry extract of red yeast rice provides direct HMG-CoA inhibition to counteract cholesterol of endogenous origin. Also, *Lespedeza capitata* extract provides for an anti-atherosclerotic action by modulating gene expression of protein. Additionally, gallic acid, catechin, epicatechin in the dry grape seed extract reduces absorption of cholesterol taken with food to counteract cholesterol of exogenous origin.

The present inventors contemplate that the policosanol affects reversible phosphorylation and protein kinases (including AMP-activated kinase) which affects HMG-CoA reductase; meanwhile, mevinolinic acid directly inhibits HMG-CoA reductase. It is believed that the combination of these ingredients produces a synergistic effect to reduce endogenous cholesterol synthesis. These four main ingredients increase the effectiveness of compositions of the present invention due to a biochemical cascade mechanism of action. Each component individually has an effect on cholesterol reduction but together they affect several different stages of cholesterol metabolism and thus significant increase the effectiveness of compositions of the present invention. It is contemplated by the inventors that the presence of policosanol increases the effectiveness of mevinolinic acid because both substances affect the same process of endogenous cholesterol synthesis. See e.g., Marazzi et al., *Long-term effects of nutraceuticals (berberine, red yeast rice, policosanol) in elderly hypercholesterolemic patients*, Istituto San Raffaele Pisana, Italy. It is also believed that the combination of these ingredients, policosanol, dry grape seed extract, and *Lespedeza capitata* extract on one hand and mevinolinic acid on the other hand produce a synergistic effect to reduce endogenous cholesterol synthesis.

The synergistic combination of policosanol, dry extracts of red rice yeast, grape seed, and *Lespedeza capitata*, provides for a higher efficiency of the inventive compositions and methods by working together to effect several levels of interruption or inhibition of the metabolic pathway during biosynthesis of cholesterol and cholesterol esters, which is unlike known products which do not provide for such a multi-pronged, of multi-faceted, approach. As a result of the synergistic action of the active ingredients of the present invention, normal blood serum LDL cholesterol concentrations may be achieved, a healthy balance between LDL and HDL may be achieved, and high triglyceride levels may be reduced.

The present invention provides naturally sourced active agents for use in the composition, that reduce the risk of statin-related side effects by, at least in part, reducing the amount of statins needed to achieve desirable cholesterol regulation. The present invention may also ensure long-lasting safety, allowing the compositions and methods disclosed herein to be included in different treatment regimens. The active ingredients of the phytoproduct potentiate its effect by simultaneously reducing endogenous cholesterol production and absorption of exogenous cholesterol, while providing anti-atherosclerotic action by modulating gene expression of proteins. The simultaneous action of the four active agent components on multiple distinct aspects of the metabolic pathway leading to biosynthesis of cholesterol and cholesterol esters results in significantly increased product efficacy whether compared to the effects imparted by each of the active agents alone or to other known products.

DETAILED DESCRIPTION

Figure 1:
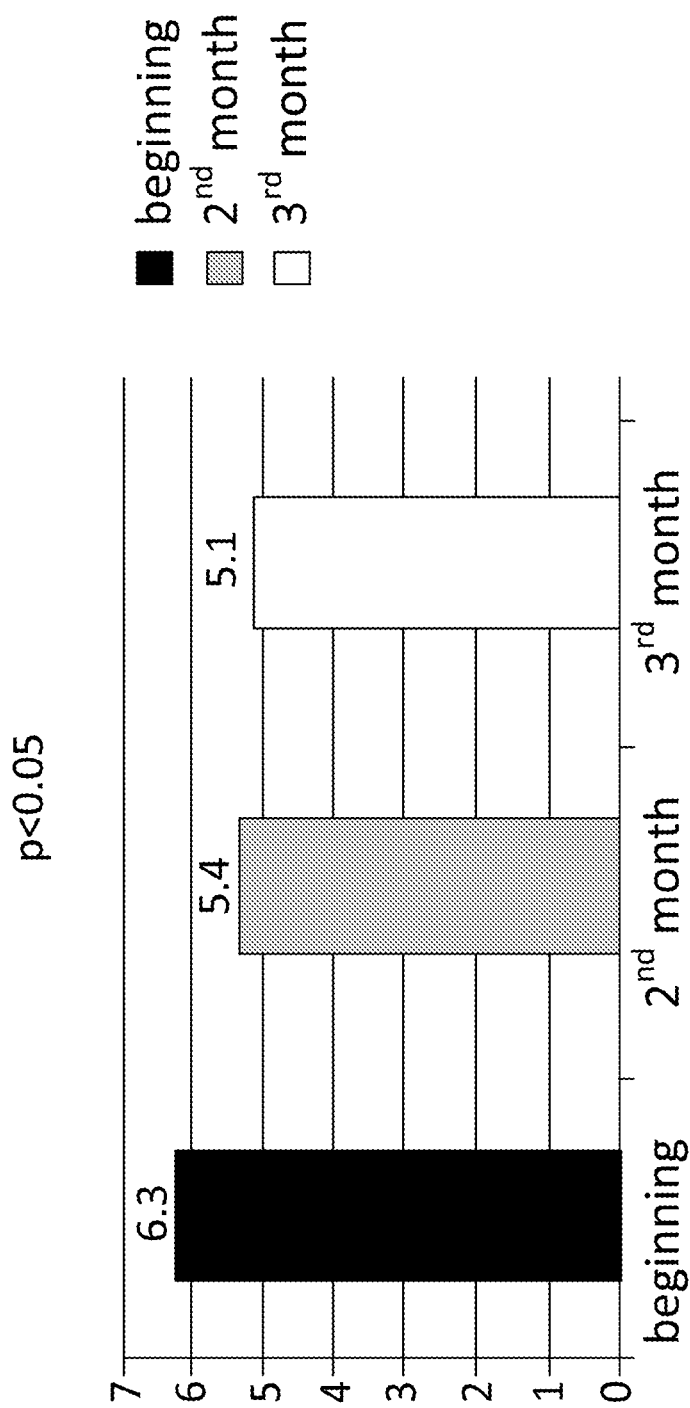
FIG. 1 illustrates the average serum total cholesterol of the study patients measured at the beginning of the study, after 60 days ("$2^{nd}$ month"), and at the end of the study after 90 days ("$3^{rd}$ month), shown in mmol/l.

The present invention includes products and methods of using products comprising natural ingredients, such as policosanol, mevinolic acid from dry yeast extract of red rice, dry extract of *Lespedeza captitata*, and dry grape seed extract, to form compositions useful for the reduction of effective doses of HMG CoA reductase inhibitors that lower cholesterol levels, i.e., statins. Additionally, the compositions and methods of the present invention beneficially allow cholesterol levels to be controlled by other mechanisms not exploited by statins, e.g., inhibiting pancreatic cholesterol and reducing the solubility of cholesterol in the mycelia.

Cholesterol

Lipoproteins are spherical macromolecular complexes, consisting of lipids and proteins. The clinically significant lipids in the blood serum include: cholesterol (esterified and non-esterified), triglycerides—triacylglycerols (molecules consisting of three fatty acids, esterified with glycerol) and phospholipids.

Cholesterol has three major functions, and takes part in the structure of the cellular wall, synthesis of steroid hormones, and formation of bile acids. The basic functions of the triglycerides are the accumulation of energy (in the fatty tissue) and the use of energy (by the muscles). Phospholipids are the basic structural material of the membranes in the organism. Fats are not soluble in plasma. Cholesterol and triglycerides become soluble by their incorporation in lipoproteins, such as the chylomicrons, lipoproteins with very low density (VLDL), lipoproteins with low density (LDL) and lipoproteins with high density (HDL). Apolipoproteins are the protein component in lipoproteins. Apolipoproteins support the lipid transportation and process their supply in three (3) ways: to serve as structural elements, to serve as receptor ligands, and to serve as regulating cofactors.

Table 3 notes basic apolipoproteins and their function.

TABLE 3

| Apolipoproteins | Function |
| --- | --- |
| Apo A-I | Structural HDL protein, activates lecithin-cholesterol acyltransferase |
| Apo A-II | Structural HDL protein |
| Apo B-48 | Structural chylomicrons protein |
| Apo B-100 | Structural VLDL, IDL, LDL protein; LDL receptor ligand |
| Apo C-II | LPL activator |
| Apo C-III | Potential inhibitor of the functions of apo C-II and apo E |
| Apo E | Ligand for the receptor of the chylomicron residual particle and for LDL receptor |
| Apo (a) | Unknown function, plasminogen antagonist |

Structure and Classification of Lipoproteins.

The mature lipoprotein particle is a sphere, containing a central nucleus of lipids (triglyceride and cholesterol ester), encircled by a monolayer surface of phospholipid, non-esterified cholesterol and apolipoproteins. For practical purposes the lipoproteins may be described on the basis of their size and density.

Chylomicrons are the largest lipoproteins. The basic structural protein is apolipoprotein B-48 (apo B-48). The larger part of the lipid nucleus (about 80%) consists of triglycerides. Synthesized and secreted by the intestines, chylomicrons transport the exogenous cholesterol, fatty acids and fat soluble vitamins which are absorbed from the digested food.

VLDLs are particles rich of triglycerides (about 80% of the lipid nucleus consists of triglycerides) and are synthesized in the liver, supply triglycerides to the periphery, and also are a precursor of intermediate density lipoproteins (IDLs) and LDLs. The basic structural protein of this particle is apo B-100.

LDLs are lipoproteins produced by processing of the residual particle of VLDLs in the liver. The nucleus is rich in cholesterol ester and forms the basic part of the blood circulating cholesterol. Here too, the basic structural protein is apo B-100, but on the surface of this particle are also detected apo CII and apo E. LDL plays a key role in the development of atherosclerosis. Lipoprotein (a) (Lp(a)) is a specific class of lipoprotein particles that are synthesized in the liver and have lipid formula similar to that of LDL. Lp(a) differ from LDL by the presence of apolipoprotein (a) (apo(a)), a protein for which structure is homologous to that of plasminogen. Apo (a) is bound by a disulfide bridge with apo B-100 and finally Lp(a) is formed. The high levels of Lp(a) are prothrombogenic and atherogenic. The plasma Lp(a) levels are basically determined by the genetic variations of Lp(a) gene.

IDLs are actually the residue of VLDLs. IDLs are formed after a part of the triglyceride in VLDL has been hydrolyzed by lipoprotein lipase. The nucleus is built by approximately 50% triglycerides and 50% cholesterol ester. On average, half of IDL particles in the human body are cleared from the plasma in the liver; the other half, after additional processing, form LDL. In clinical practice, the assessment of cholesterol levels includes its measurement both in LDL and IDL fractions.

HDLs are formed by non-esterified cholesterol and a phospholipid, taken from the peripheral tissues and from the surface of the lipoproteins rich in triglycerides. The basic structural protein is apo A-I, the nucleus is basically a cholesterol ester. HDLs mediate the return of lipoproteins and tissue cholesterol to the liver for excretion, a process known as reverse cholesterol transportation. Another function of HDLs is to transfer apo E and apo C-II to the chylomicrons and VLDL.

LDL catabolism occurs where Apo B-100 on the LDL surface is bound to the LDL cellular receptor, after that LDL is absorbed in the cell, where it is catabolized. After hydrolysis of the nuclear lipids, the non-esterified cholesterol is used by the cells for synthesis of membranes, bile acids, and steroid hormones as well as for various regulatory actions that prevent the excessive accumulation of cholesterol in the cell. Most of the LDL particles in the plasma are absorbed by the liver through the LDL receptor.

Hepatic lipase transforms VLDL to LDL and HDL.

Active Agents

1. Policosanol

Policosanol, in a preferred embodiment of the present invention, is a natural mixture of aliphatic primary alcohols isolated from purified sugar cane wax (*Saccharum officinarum L.*) by hydrolytic cleavage and subsequent purification. The chemical formula is $CH_3-(CH_2)_n-CH_2OH$, having a chain length ranging from 24 to 34 carbon atoms.

Octacosanol (over 50%), triacontanol and hexacosanol are the main ingredients of policosanol. In a preferred embodiment of the present invention, the policosanol comprises about 51.54% octacosanol, about 24.43% triacontanol, and about 15.80% hexacosanol.

Because policosanol is naturally sourced, i.e., it comes from sugar cane wax, it provides an attractive alternative for patients who are reluctant to use chemically-produced drugs for the prevention and treatment of hypercholesterolemia. In a preferred embodiment of the present invention, the policosanol is sourced from sugar cane stems and comprises policosanol in amounts greater than or equal to 95% wherein the octacosanol component is present in amounts greater than or equal to 50%.

From the analysis of 52 publications, scientists came to the conclusion that policosanol (with the essential octacosanol component) favorably alters the lipid profile, approaching the effectiveness of hypolipidemic drugs. See e.g., Chen et al., *Meta-Analysis of Natural Therapies for Hyperlipidemia: Plant Sterols and Stanols versus Policosanol*, SCHOOL OF PHARMACY AND PHARMACAL SCIENCES, PURDUE UNIVERSITY, WEST LAFAYETTE, INDIANA 47907-2091. Its safety and good tolerance have also been proven. See Gouni-Berthold et al., *Policosanol: clinical pharmacology and therapeutic significance of a new lipid-lowering agent*, MEDICAL POLICLINIC, UNIVERSITY OF BONN, BONN, GERMANY. Policosanol has been shown to have cholesterol-lowering properties clinically comparable to the effects of low-dose statins. Policosanol has been shown to reduce cholesterol in animal models, healthy volunteers, and type II hypercholesterolemia patients. See e.g., Chen et al., *Meta-Analysis of Natural Therapies for Hyperlipidemia: Plant Sterols and Stanols versus Policosanol*, SCHOOL OF PHARMACY AND PHARMACAL SCIENCES, PURDUE UNIVERSITY, WEST LAFAYETTE, INDIANA 47907-2091. Hyperlipidemias are also classified according to which types of lipids are elevated, that is hypercholesterolemia, hypertriglyceridemia or both in combined hyperlipidemia. Elevated levels of lipoprotein (a) may also be classified as a form of hyperlipidemia. Guardamagna et al., *The treatment of hypercholesterolemic children: Efficacy and safety of a combination of red yeast rice extract and policosanols*, DEPARTMENT OF PEDIATRICS, UNIVERSITY OF TURIN, PIAZZA POLONIA, 94, I-10126 TURIN, ITALY.

Policosanol also has anti-platelet effects as well as the ability to prevent lipoprotein peroxidation. Taylor et al, *Octacosanol in Human Health*, SCHOOL OF PHARMACY AND PHARMACEUTICAL SCIENCES, UNIVERSITY OF MANCHESTER, MANCHESTER, UNITED KINGDOM. Advantages of policosanol are its good tolerability and extremely low incidence of adverse events (side effects), which does not require frequent laboratory tests.

The exact mechanism of action of policosanol for lipid lowering has not been sufficiently elucidated, but has been associated with suppression of cholesterol synthesis as well as stimulation of the degradation of LDL cholesterol in liver cells by activating lipases. Singh et al, *Policosanol Inhibits Cholesterol Synthesis in Hepatoma Cells by Activation of AMP-Kinase*, PHARMACEUTICAL SCIENCES, COLLEGE OF PHARMACY, UNIVERSITY OF KENTUCKY, LEXINGTON, KENTUCKY May 18, 2006. Suppression of platelet aggregation is believed to be associated with the effect of prostaglandin synthesis. That is, it lowers the level of thromboxane A2 in the serum and increases prostacyclin level. It also reduces the risk of thrombosis.

HMG-CoA reductase has been shown to be subject to regulation by reversible phosphorylation by several protein kinases, including AMP-activated kinase, a protein kinase C, and a calmodulin-dependent protein kinase. Singh et al, *Policosanol Inhibits Cholesterol Synthesis in Hepatoma Cells by Activation of AMP-Kinase*, PHARMACEUTICAL SCIENCES, COLLEGE OF PHARMACY, UNIVERSITY OF KENTUCKY, LEXINGTON, KENTUCKY May 18, 2006. AMP-kinase, which also inactivates acetyl-CoA carboxylase, is the major regulator of HMG-CoA reductase phosphorylation, and its co-regulation of acetyl-CoA carboxylase suggests coordinated regulation of cholesterol and fatty acid biosynthesis. AMP-kinase is activated by 5-adenosine monophosphate, which increases in cells during ATP depletion as a consequence of various stresses (hypoxia, ischemia, and glucose depletion) and excessive energy demands. Activation of AMP-kinase requires phosphorylation of the catalytic unit by one or more upstream kinases and indeed, long-chain fatty acids per se seem to activate AMP-kinase via a phosphorylation mechanism.

Some studies demonstrate that policosanol promotes the phosphorylation of AMP-kinase in hepatoma cells, suggesting that this is the likely mechanism by which HMG-CoA reductase activity is reduced in treated cells. Singh et al, *Policosanol Inhibits Cholesterol Synthesis in Hepatoma Cells by Activation of AMP-Kinase*, PHARMACEUTICAL SCIENCES, COLLEGE OF PHARMACY, UNIVERSITY OF KENTUCKY, LEXINGTON, KENTUCKY May 18, 2006. Policosanol decreased acetate incorporation into cholesterol without affecting the incorporation of mevalonate, indicating that these compounds act at or above HMG-CoA reductase. That is, policosanol interrupts or inhibits the metabolic pathway at a point earlier than or preceding any action by HMG-CoA reductase.

Policosanol did not directly inhibit HMG-CoA reductase, and incubation of these compounds with hepatoma cells did not affect reductase enzyme levels. It remains unclear whether the very long-chain alcohols in policosanol must first undergo oxidative metabolism via the fatty alcohol cycle to the corresponding fatty acids or subsequent peroxisomal-oxidation. Pharmacokinetic studies on octacosanol metabolism have indicated that this very long-chain alcohol can undergo oxidation to $CO_2$ in vivo, presumably via this pathway.

Because AMP-kinase is activated by phosphorylation and is known to suppress HMG-CoA reductase activity, these results suggest that policosanol or a policosanol-associated metabolite decreases HMG-CoA reductase activity by activating AMP-kinase. Singh et al, *Policosanol Inhibits Cholesterol Synthesis in Hepatoma Cells by Activation of AMP-Kinase*, PHARMACEUTICAL SCIENCES, COLLEGE OF PHARMACY, UNIVERSITY OF KENTUCKY, LEXINGTON, KENTUCKY May 18, 2006.

A main component of policosanol is octacosanol (CH3[CH2]26CH2014, a high molecular weight primary aliphatic alcohol. Octacosanol has many uses for treating various conditions. The most widely studied uses relate to their cholesterol-lowering properties and many studies have shown that octacosanol is very effective in lowering LDL and increasing HDL. Taylor et al, *Octacosanol in Human Health*, SCHOOL OF PHARMACY AND PHARMACEUTICAL SCIENCES, UNIVERSITY OF MANCHESTER, MANCHESTER, UNITED KINGDOM.

A number of studies have shown that octacosanol (as part of policosanol) is as effective as aspirin in its anti-aggregative effects. Taylor et al, *Octacosanol in Human Health*, SCHOOL OF PHARMACY AND PHARMACEUTICAL SCIENCES, UNIVERSITY OF MANCHESTER, MANCHESTER, UNITED KINGDOM. Octacosanol may be given to patients with high LDL cholesterol and hypertension or a high risk of clotting.

Octacosanol (in policosanol) also offers cytoprotective effects. This allows the administration of octacosanol as an alternative to aspirin in patients who have a history of or have stomach irritation. Thus octacosanol can be an ideal alternative in three types of conditions that usually occur at the same time. That is, for subjects with high LDL cholesterol in connection with hypertension requiring anti-aggregant, but wherein the subject also suffers from stomach irritation.

There have been studies exploring combinations of octacosanol with other treatments. Guardamagna et al., *The treatment of hypercholesterolemic children: Efficacy and safety of a combination of red yeast rice extract and policosanols*, DEPARTMENT OF PEDIATRICS, UNIVERSITY OF TURIN, PIAZZA POLONIA, 94, 1-10126 TURIN, ITALY LIPID CLINIC RESEARCH, DEPARTMENT OF PEDIATRICS, UNIVERSITY OF ROME "LA SAPIENZA", ITALY. For example, if the statin (or other HMG-CoA inhibitor like mevinolinic acid) was taken with octacosanol, the combined effects could be extremely beneficial because LDL cholesterol levels will almost certainly be lowered. If octacosanol should be taken with anticoagulation therapy, such as warfarin or aspirin, synergistic action and potency enhancement should be considered.

Octacosanol has the potential to treat many conditions without identified side effects at the recommended doses and would thus be useful for many patients. In a preferred embodiment, a recommended dose of policosanol (comprising a minimum amount of 50% octacosanol), is equal to or greater than about 10 mg/day. There are also possibilities for taking octacosanol as a double-action treatment for hypertension and high cholesterol without gastric irritation or muscle problems. This could be an important product for the future, with the growing problem of obesity and the increased risk of atherosclerosis and CVD (cardiovascular diseases) worldwide.

The policosanol component is included in the formulations of the present invention because it is contemplated by the inventors to significantly contribute to increasing the effectiveness of the inventive compositions described herein due to its biochemical cascade mechanism of action with the other components in the direction of lowering LDL cholesterol.

2. Red Rice Yeast

Another component for lipid regulation is the monacolin spectrum in red rice yeast which contains several types of monacolins that competitively inhibit 3-hydroxy-3-methylglutaryl-coenzyme A reductase (HMG-CoA reductase) in the liver. HMG-CoA reductase converts 3-hydroxy-3-methylglutaryl-coenzyme A into mevalonate. See also, L Jing et al., *Comparison of the efficacy and safety of xuezhikang and lovastatin in hyperlipidemic patients with hypertension*, JOURNAL OF CLINICAL EPIDEMIOLOGY (1999).

The dry extract of red rice yeast is obtained by fermentation of rice with red yeast (*Monascus purperus*). It may contain monacolin K (3.12%), mevinolinic acid and lovastatin, which have a direct effect on the metabolism of cholesterol.

In a preferred embodiment, the dry extract of red rice yeast used to produce compositions of the present invention have a greater relative percentage of mevinolinic acid and a lower relative percentage of, or only traces of, lovastatin when compared to other dry extracts of red yeast rice.

One monacolinic molecule may, during its active reaction time, displace 10,000 molecules of 3-hydroxy-3-methylglutaryl coenzyme A such that HMG-CoA reductase is occupied with "placebo" activity. This "trick" results in a reduction in cholesterol production.

Monacolins do not completely block production of the basic structures required for cholesterol synthesis, but only interrupt or reduce such production. Therefore, they are also referred to as competitive HMG-CoA reductase inhibitors. Their action is reversible and decreases over time. The period of their half-life is about 1.3 hours to about 2 hours, and their action begins in about 30-60 minutes.

Mevinolinic acid directly affects HMG-CoA reductase. Due to the advantages of mevinolinic acid to lovastatin (a prodrug), lovastatin is not present, or is not present in significant amounts, in the inventive compositions and methods. Mevinolinic acid is a direct inhibitor of HMG-CoA reductase (unlike lovastatin), which makes it well-suited for use with the present invention. Mevinolinic acid is a hydrophilic molecule and therefore is minimally distributed in non-liver cells which, in turn, leads to a reduction in the risk of developing myopathy and other side effects. Treatment with products that inhibit HMG-CoA reductase, such as mevinolinic acid, lowers LDL cholesterol levels without leading to severe depletion of this metabolite and does not endanger the body by reducing cholesterol required for vital functions such as cell membrane structure, steroid hormones synthesis and bile acids. Grundy et al, *Inhibition of 3-hydroxy-3-methylglutaryl-CoA reductase by mevinolin in familial hypercholesterolemia heterozygotes: effects on cholesterol balance*, PROCEEDING OF THE NATIONAL ACADEMY OF SCIENCES OF THE UNITES STATES OF AMERICA (PNAS) (1984).

Mevinolinic acid (betahydroxy butyric) competitively inhibits HMG-CoA reductase and lowers cholesterol concentration by preventing the conversion of HMG-CoA to mevalonate. This reduces plasma cholesterol levels and the concentration of LDL, which contain high cholesterol. The amount of apolipoprotein B, which is mainly found in LDL, is also reduced.

Pharmacology of Mevinolinic Acid Compared to Lovastatin

Because the structural formula of mevinolinic acid is close to that of lovastatin, attention should be given to the main differences between them. One difference arises because of an additional $H_2O$ molecule in mevinolinic acid, which leads to significant differences in action.

In aqueous-acidic medium, lovastatin is converted primarily into the hydroxyacid form, and the dynamic equilibrium between mevinolinic acid and lovastatin is significantly shifted in favor of mevinolinic acid. The reason for this is that the lactonization of mevinolinic acid in lovastatin requires energy (4.93 kcal/Mol), while the reverse process (hydrolysis of mevinolinic acid in lovastatin) releases 2.42 kcal/Mol.

When the lactone lovastatin is placed in an aqueous-acidic medium (e.g., gastric juice), it is hydrolyzed alone without the presence of enzymes to a certain percentage in mevinolinic acid, but in these circumstances the mevinolinic acid can be converted back into the lactone form.

Mevinolinic acid dissolves easily in water, but with more difficultly in fat. Lactone lovastatin is difficult to dissolve in water but dissolves more easily in fat. These solubility properties are determined by the open (mevinolinic acid) or closed (lovastatin) lactone ring. Mevinolinic acid is absorbed from the digestive tract up to about 83% to 100%. By contrast, lactone lovastatin is absorbed from the digestive tract up to about only 30% (Reynoso et al., *Preclinical pharmacokinetics of statins* (2002)).

The significant difference between mevinolinic acid and lovastatin is in pharmacological action. Lovastatin is inactive and only after conversion to mevinolinic acid is converted into an active effective form. Methylvinyl is an open lactone ring, making it directly into an active component, i.e., mevinolinic acid, which directly inhibits HMG-CoA reductase in the liver.

The lovastatin molecule is a lipophilic molecule, and since only about 30% of it (as noted above) is converted to beta hydroxyl acid, the remaining amount is absorbed by the cells in the body, which in turn gives rise to undesirable side effects. By contrast, mevinolinic acid is a hydrophilic molecule that is directly digested by hepatocytes, as they are the only cells whose transport system allows its absorption. Endo et al, *Biochemical aspect of HMG CoA reductase inhibitors*, DEPARTMENT OF AGRICULTURAL AND BIOLOGICAL CHEMISTRY, TOKYO NOKO UNIVERSITY, FUCHU, TOKYO, JAPAN (1989). This helps avoid undesirable side effects associated with the accumulation of lovastatin molecules in non-target cells and cellular structures.

As described above, lovastatin is activated slowly and only partially. Initially, a portion of it disintegrates non-enzymatically in the stomach, and another portion of it is enzymatically converted to mevinolinic acid. The remaining lovastatin works only when chemically activated in the liver by the enzyme CYP3A4 from the cytochrome P450 enzyme system. Then three different hydroxy acid and lactone forms of lovastatin originate, namely those of 6'-beta-hydroxy-lovastatin, 3'-hydroxy-lovastatin and 6'-exomethylene lovastatin. While natural mevinolinic acid acts directly as an inhibitor of HMG-CoA reductase, lovastatin is first converted into at least seven structures in order to act.

There are clinical trials that confirm the difference in the speed and magnitude of the effects of lovastatin and monacolins in red rice yeast. Ling et al, *Comparison of the efficacy and safety of xuezhikang and lovastatin in hyperlipidemic patients with hypertension*, JOURNAL OF CLINICAL EPIDEMIOLOGY, PERGAMON (1999). It has been found in a comparative study that the total cholesterol values have reduced by 20.8% on intake of 10 mg red rice yeast for 8 weeks, whereas for the same time, the intake of 20 mg of lovastatin leads to a 19% reduction in cholesterol. The present inventors contemplate that the reason for this favorable comparison is the presence of mevinolinic acid from the group of monacolins in red rice yeast. Thus, from this study, the present inventors reason that a 10 mg daily monacolin blend (with a higher amount of mevinolinic acid) may act as 20 mg of lovastatin. This result is explained by the better availability of a large amount of natural mevinolinic acid in red rice yeast compared to the synthetic form of lovastatin. The cholesterol-lowering values do not differ significantly from each other, but it is clear that red rice yeast acts in smaller doses and more directly compared to lovastatin. This makes the natural products with a higher amount of mevinolinic acid significantly more efficient. Mevinolinic acid should not be confused with lovastatin. These two substances are well distinguished because the difference between them, i.e., the presence of a single additional water molecule in mevinolinic acid, results in a significant difference in performance and effectiveness. In comparison to lovastatin, mevinolinic acid, as a key part of natural monacolins present in red rice yeast, acts far more optimally pharmacologically.

3. Grape Seed Extract (Gallic Acid Catechin, Epicatechin)

The grape seed extract of the present invention contains more than 95% proanthocyanidins, containing catechin, epicatechin, gallic acid. In a preferred embodiment, the grape seed extract used with the present invention includes proanthocyanidins in amounts greater than or equal to 95%.

The oral administration of grape seed extract with high fat emulsion provided by, for example, food in a subject's stomach or intestines, reduces cholesterol levels in blood due to the presence of gallic acid, catechin and epicatechin which suppress cholesterol absorption by reducing cholesterol micellization and inhibiting pancreatic cholesterol esterase resulting in limiting absorption of cholesterol when taken with food (exogenous) and a decrease in total serum cholesterol.

This reduction in cholesterol value in gallic acid mycelium, catechin and epicatechin is believed to be related to changes in the structure of mycelial cholesterol.

The major polyphenols in grape seed extract provide significant benefits to human health in the prevention of dyslipidemia and cardiovascular disease. Ngamukote S et al., *Cholesterol-lowering activity of the major polyphenols in grape seed*, THE MEDICAL FOOD RESEARCH AND DEVELOPMENT CENTER, DEPARTMENT OF TRANSFUSION MEDICINE, FACULTY OF ALLIED HEALTH SCIENCES, CHULALONGKORN UNIVERSITY, BANGKOK, THAILAND (2011).

In a number of studies, cholesterol is shown to be lowered by the action of three major polyphenols contained in grape seed. The results show that gallic acid, catechin and epicatechin significantly inhibit pancreatic cholesterol ester depending on their concentration. Ngamukote S et al., *Cholesterol-lowering activity of the major polyphenols in grape seed*, THE MEDICAL FOOD RESEARCH AND DEVELOPMENT CENTER, DEPARTMENT OF TRANSFUSION MEDICINE, FACULTY OF ALLIED HEALTH SCIENCES, CHULALONGKORN UNIVERSITY, BANGKOK, THAILAND (2011). Moreover, they bind to taurocholic acid, taurodeoxycholic acid and glyco-deoxycholic acid at levels ranging from 38.6% to 28.2%. At a concentration of 0.2 mg/mL gallic acid, catechin, and epicatechin reduce the formation of lipoprotein mycelia by 27.26±2.17%, 11.88±0.75% and 19.49±3.71%, respectively. These results clearly demonstrate that the three major polyphenol compounds contained in the grape seed extract have proven cholesterol-lowering action by inhibiting pancreatic cholesterol esterase, bile acid binding, and cholesterol mycelium reduction, resulting in reduced cholesterol absorption.

Gallic acid, catechin and epicatechin inhibit cholesterol esterase. In general, pancreatic cholesterol esterase plays an important role in the hydrolysis of cholesterol esters (via food), which release free cholesterol into the intestinal lumen. It also improves the inclusion of cholesterol in mixed micelles and the transport of free cholesterol to enterocytes.

Inhibition of cholesterol esterase is expected to reduce the absorption of cholesterol taken with food, and this in turn has an effect on the reduction in total serum cholesterol. Up to 15% of blood serum cholesterol is derived from food (exogenous), the rest is the result of endogenous synthesis.

These three polyphenols have been studied to inhibit pancreatic cholesterol esterase, which leads to increased control of food-borne cholesterol derivatives and restriction of free cholesterol in the blood stream. Ngamukote S et al., *Cholesterol-lowering activity of the major polyphenols in grape seed*, THE MEDICAL FOOD RESEARCH AND DEVELOPMENT CENTER, DEPARTMENT OF TRANSFUSION MEDICINE, FACULTY OF ALLIED HEALTH SCIENCES, CHULALONGKORN UNIVERSITY, BANGKOK, THAILAND (2011). They also bind to bile acids, which reduces the solubility of cholesterol in the micelles.

Flavonoids and their derivatives, such as anthocyanins, may be used to control cholesterol levels. Reducing "bad" cholesterol and increasing levels of protective "good" cholesterol have been repeatedly studied and demonstrated after oral administration of anthocyanins. Qin et al., *Anthocyanin supplementation improves serum LDL-and HDL-cholesterol concentrations associated with the inhibition of cholesteryl ester transfer protein in dyslipidemic subjects*, THE AMERICAN JOURNAL OF CLINICAL NUTRITION, AMERICAN SOCIETY FOR NUTRITION (2009).

Multiple studies have shown many positive effects associated with the prevention of atherosclerosis when taking these substances. Proanthocyanidins in dry grape seed extract also protect against cardiovascular disease, improving not only lipid homeostasis but also with their antioxidant and anti-inflammatory properties. Simultaneously with decreasing plasma levels of atherogenic lipoproteins LDL, they also increase antiatherogenic HDL cholesterol. Studies have shown that proanthocyanidins act primarily on intestinal lipid absorption, chylomicron secretion by the intestine and VLDL by the liver. These processes are most repressed by proanthocyanidins, which therefore, induce hypolipidemic effects.

4. Dry Extract of *Lespedeza capitata*

Dry extract of *Lespedeza capitata* contains several biologically active ingredients. Research has confirmed high levels of flavonoids and linked polyphenol compounds. In a preferred embodiment, the dry extract of *Lespedeza capitata* used in the present invention is from the stem and leaf of the plant.

The antioxidant component kaempferitrin is isolated, along with other flavonoids. Kaempferitrin or kaempferol-3,7-dihramnoside is of particular importance for the prevention of cardiovascular disease. Kaempferol 3,7-dirhamnoside found in the *Lespedeza capitata* is a yellow compound with a low molecular weight (molecular weight of 286.2 g/mol) and is a common natural flavonoid. This flavonoid is widespread in many plant-derived foods and traditional medicine. Kaempferol and its glycosides have many different pharmacological activities, such as antioxidant, anti-inflammatory, anticancer, antimicrobial, neuroprotective, antidiabetic, etc.

Studies have shown that kaempferol is a potent and effective agent against atherosclerosis. Kong et al., *The anti-inflammatory effect of kaempferol on early atherosclerosis in high cholesterol fed rabbits* (2013). So far, studies on the anti-oxidant, anti-inflammatory and cardioprotective effect of kaempferol are primarily linked to endothelial cells in vitro.

A number of studies have been carried out to evaluate the efficacy of kaempferol on inflammatory molecules such as E-selectin, intercellular adhesion molecule-1 (ICAM-1), vascular cellular adhesion molecule-1 (VCAM-1) and monocyte chemotaxis protein 1 (MCP-1) in induced high-cholesterol atherosclerosis. Studies conclude that Kaempferol 3,7-dirhamnoside shows anti-atherosclerotic action by modulation of gene expression of protein. Kong et al., *The anti-inflammatory effect of kaempferol on early atherosclerosis in high cholesterol fed rabbits* (2013).

Manufacture

In a preferred embodiment, the policosanol and dry extracts of the aforementioned active substances are mixed in a stainless reactor in the aforementioned ratios and the resulting mixture is homogenized to obtain a homogeneous product.

In an alternative embodiment, inactive components are added and homogenized along with the active substances. Inactive components such as, for example, microcrystalline cellulose, polyvinylpyrrolidone, magnesium stearate, talc, film coating (e.g., polyvinyl alcohol, titanium dioxide color, polyethylene glycol, and talc), may be used to stabilize the formulation active agents. In certain embodiments, the inventive formulations described herein include microcrystalline cellulose, polyvinylpyrrolidone, magnesium stearate, talc, film coating (e.g., polyvinyl alcohol, titanium dioxide color, polyethylene glycol, and talc). The inventors note, however, that the selection of excipients used with the invention described herein may vary. In one embodiment, specific technological processes may be guaranteed by GMP, HACCP, ISO and/or EU certificate of conformity.

Certain embodiments of the present invention use Nutraficient® (made by Colorcon® company), a food supplement coating designed as an immediate release coating system specifically for nutritional, herbal and dietary supplements. This coating not only provides moisture protection but also helps overcome unpleasant tastes and odors.

In a preferred embodiment, the mixture is dispensed into capsules. The capsules may be formed from hydroxypropylmethylcellulose, pullulan, gelatin, starch, cellulose, or any other appropriate material. In a preferred embodiment, the capsules are formed from hydroxypropylmethylcellulose, such as the Vcaps® Plus capsule manufactured by Capsugel®. The capsule provides moisture protection and helps overcome unpleasant tastes and odors, and also facilitates swallowing, as the products and methods of the present invention may be taken or practiced for a long time.

In a preferred embodiment, a dosage form may be a capsule and may contain the following biologically active substances: about 10 mg policosanol, about 330 mg dry extract of red rice yeast, about 240 mg dry extract of *Lespedeza capitata*, and about 120 mg dry grape seed extract. Accordingly, dosage forms, such as capsules according to the present invention are expected to be greater than 600 mg in weight. In a preferred embodiment, the weight of the dosage forms described herein ranges from about 600 mg to about 800 mg without the capsule, and from about 800 mg to about 1000 mg with the capsule. For example, the weight of the dosage forms described herein, without the capsule, may range from about 600 mg to about 650 mg, from about 600 mg to about 700 mg, from about 600 mg to about 750 mg, from about 600 mg to about 800 mg, from about 650 mg to about 700 mg, from about 650 mg to about 750 mg, from about 650 mg to about 800 mg, from about 700 mg to about 750 mg, from about 700 mg to about 800 mg, or from about 750 mg to about 800 mg; and the weight of the dosage form described herein, with the capsule, may range from about 800 mg to about 850 mg, from about 800 mg to about 900 mg, from about 800 mg to about 950 mg, from about 800 mg to about 1000 mg, from about 850 mg to about 900 mg, from about 850 mg to about 950 mg, from about 850 mg to about 1000 mg, from about 900 mg to about 950 mg, from about 900 mg to about 1000 mg, or from about 950 mg to about 1000 mg. In an alternative embodiment, the weight of the dosage forms described herein ranges from about 700 mg to about 850 mg without the capsule, and from about 900 mg to about 1050 mg with the capsule. For example, the weight of the dosage forms described herein, without the capsule, may range from about 700 mg to about 750 mg, from about 700 mg to about 800 mg, from about 700 mg to about 850 mg, from about 750 mg to about 800 mg, from about 800 mg to about 850 mg, or from about 700 mg to about 800 mg; and the weight of the dosage form described herein, with the capsule, may range from about 900 mg to about 950 mg, from about 900 mg to about 1000 mg, from about 900 mg to about 1050 mg, from about 950 mg to about 1000 mg, from about 950 mg to about 1050 mg, from about 1000 mg to about 1050 mg, or from about 900 mg to about 1000 mg.

In another preferred embodiment, a dosage form may be a capsule and may contain the following biologically active substances: about 10 mg policosanol, about 700 mg dry extract of red rice yeast, about 240 mg dry extract of *Lespedeza capitata*, and about 120 mg dry grape seed extract. Accordingly, dosage forms, such as capsules according to the present invention are expected to be greater than 800 mg in weight. In a preferred embodiment, the weight of the dosage forms described herein ranges from about 800 mg to about 1200 mg without the capsule, and from about 1000 mg to about 1500 mg with the capsule. For example, the weight of the dosage forms described herein, without the capsule, may range from about 800 mg to about 850 mg, from about 800 mg to about 900 mg, from about 800 mg to about 950 mg, from about 800 mg to about 1000 mg, from about 800 mg to about 1050 mg, from about 800 mg to about 1100 mg, from about 800 mg, to about 1150 mg, from about 800 mg to about 1200 mg, from about 850 mg to about 900 mg, from about 850 mg to about 950 mg, from about 850 mg to about 1000 mg, from about 850 mg to about 1050 mg, from about 850 mg to about 1100 mg, from about 850 mg to about 1150 mg, from about 850 mg to about 1200 mg, from about 900 mg to about 950 mg, from about 900 mg to about 1000 mg, from about 900 mg to about 1050 mg, from about 900 mg to about 1100 mg, from about 900 mg to about 1150 mg, from about 900 mg to about 1200 mg, from about 950 mg to about 1000 mg, from about 950 mg to about 1050 mg, from about 950 mg to about 1100 mg, from about 950 mg to about 1150 mg, from about 950 mg to about 1200 mg, from about 1000 mg to about 1050 mg, from about 1000 mg to about 1100 mg, from about 1000 mg to about 1150 mg, from about 1000 mg to about 1200 mg, from about 1050 mg to about 1100 mg, from about 1050 mg to about 1150 mg, from about 1050 mg to about 1200 mg, from about 1100 mg to about 1150 mg, from about 1100 mg to about 1200 mg, or from about 1150 mg to about 1200 mg; and the weight of the dosage form described herein, with the capsule, may range from about 1000 mg to about 1050 mg, from about 1000 mg to about 1100 mg, from about 1000 mg to about 1150 mg, from about 1000 mg to about 1200 mg, from about 1000 mg to about 1250 mg, from about 1000 mg to about 1300 mg, from about 1000 mg to about 1350 mg, from about 1000 mg to about 1400 mg, from about 1000 mg to about 1450 mg, from about 1000 mg to about 1500 mg, from about 1050 mg to about 1100 mg, from about 1050 mg to about 1150 mg, from about 1050 mg to about 1200 mg, from about 1050 mg to about 1250 mg, from about 1050 mg to about 1300 mg, from about 1050 mg to about 1350 mg, from about 1050 mg to about 1400 mg, from about 1050 mg to about 1450 mg, from about 1050 mg to about 1500 mg, from about 1100 mg to about 1150 mg, from about 1100 mg to about 1200 mg, from about 1100 mg to about 1250 mg, from about 1100 mg to about 1300 mg, from about 1100 mg to about 1350 mg, from about 1100 mg to about 1400 mg, from about 1100 mg to about 1450 mg, from about 1100 mg to about 1500 mg, from about 1150 mg to about 1200 mg, from about 1150 mg to about 1250 mg, from about 1150 mg to about 1300 mg, from about 1150 mg to about 1350 mg, from about 1150 mg to about 1400 mg, from about 1150 mg to about 1450 mg, from about 1150 mg to about 1500 mg, from about 1200 mg to about 1250 mg, from about 1200 mg to about 1300 mg, from about 1200 mg to about 1350 mg, from about 1200 mg to about 1400 mg, from about 1200 mg to about 1450 mg, from about 1200 mg to about 1500 mg, from about 1250 mg to about 1300 mg, from about 1250 mg to about 1350 mg, from about 1250 mg to about 1400 mg, from about 1250 mg to about 1450 mg, from about 1250 mg to about 1500 mg, from about 1300 mg to about 1350 mg, from about 1300 mg to about 1400 mg, from about 1300 mg to about 1450 mg, from about 1300 mg to about 1500 mg, from about 1350 mg to about 1400 mg, from about 1350 mg to about 1450 mg, from about 1350 mg to about 1500 mg, from about 1400 mg to about 1450 mg, from about 1400 mg to about 1500 mg, or from about 1450 mg to about 1500 mg.

The inventors contemplate that the dosage forms used to deliver an effective amount of the compositions of the present invention may be divided or delivered between two, three, four, or five, etc., dosage forms such as capsules at each oral dosing.

In an alternative embodiment, the mixture is compressed into tablets. The tablets are a homogeneous mixture, granulated, compressed and film coated. The tablet is film coated to avoid bad taste and to facilitate swallowing as the products and methods of the present invention may be taken or practiced for a long time.

In an alternative embodiment, a dosage form may be a tablet and may contain the following biologically active substances: about 10 mg policosanol, about 700 mg dry extract of red rice yeast, about 240 mg dry extract of Lespedeza capitata, and about 120 mg dry grape seed extract. Accordingly, dosage forms, such as tablets, according to the present invention are expected to be greater than 900 mg in weight. In one embodiment, dosage forms, such as tablets, according to the present invention are expected to be greater than about 1070 mg in weight. In another embodiment, the weight of the dosage forms described herein ranges from about 960 mg to about 1500 mg. For example, the weight of the dosage forms described herein may range from may range from about 960 mg, to about 1000 mg, from about 960 mg to about 1050 mg, from about 960 mg to about 1100 mg, from about 960 mg to about 1150 mg, from about 960 mg to about 1200 mg, from about 960 mg to about 1200 mg, from about 960 mg to about 1250 mg, from about 960 mg to about 1300 mg, from about 960 mg to about 1350 mg, from about 960 mg to about 1400 mg, from about 960 mg to about 1450 mg, from about 960 mg to about 1500 mg, from about 1000 mg to about 1050 mg, from about 1000 mg to about 1100 mg, from about 1000 mg to about 1150 mg, from about 1000 mg to about 1200 mg, from about 1000 mg to about 1250 mg, from about 1000 mg to about 1300 mg, from about 1000 mg to about 1350 mg, from about 1000 mg to about 1400 mg, from about 1000 mg to about 1450 mg, from about 1000 mg to about 1500 mg, from about 1050 mg to about 1100 mg, from about 1050 mg to about 1150 mg, from about 1050 mg to about 1200 mg, from about 1050 mg to about 1250 mg, from about 1050 mg to about 1300 mg, from about 1050 mg to about 1350 mg, from about 1050 mg to about 1400 mg, from about 1050 mg to about 1450 mg, from about 1050 mg to about 1500 mg, from about 1100 mg to about 1150 mg, from about 1100 mg to about 1200 mg, from about 1100 mg to about 1250 mg, from about 1100 mg to about 1300 mg, from about 1100 mg to about 1350 mg, from about 1100 mg to about 1400 mg, from about 1100 mg to about 1450 mg, from about 1100 mg to about 1500 mg, from about 1150 mg to about 1200 mg, from about 1150 mg to about 1250 mg, from about 1150 mg to about 1300 mg, from about 1150 mg to about 1350 mg, from about 1150 mg to about 1400 mg, from about 1150 mg to about 1450 mg, from about 1150 mg to about 1500 mg, from about 1200 mg to about 1250 mg, from about 1200 mg to about 1300 mg, from about 1200 mg to about 1350 mg, from about 1200 mg to about 1400 mg, from about 1200 mg to about 1450 mg, from about 1200 mg to about 1500 mg, from about 1250 mg to about 1300 mg, from about 1250 mg to about 1350 mg, from about 1250 mg to about 1400 mg, from about 1250 mg to about 1450 mg, from about 1250 mg to about 1500 mg, from about 1300 mg to about 1350 mg, from about 1300 mg to about 1400 mg, from about 1300 mg to about 1450 mg, from about 1300 mg to about 1500 mg, from about 1350 mg to about 1400 mg, from about 1350 mg to about 1450 mg, from about 1350 mg to about 1500 mg, from about 1400 mg to about 1450 mg, from about 1400 mg to about 1500 mg, or from about 1450 mg to about 1500 mg.

In an another alternative embodiment, a dosage form may be a tablet and may contain the following biologically active substances: about 10 mg policosanol, about 330 mg dry extract of red rice yeast, about 240 mg dry extract of Lespedeza capitata, and about 120 mg dry grape seed extract. Accordingly, dosage forms, such as tablets, according to the present invention are expected to be greater than 600 mg in weight. In one embodiment, dosage forms, such as tablets, according to the present invention are expected to be greater than about 800 mg in weight. In another embodiment, the weight of the dosage forms described herein ranges from about 800 mg to about 1200 mg. For example, the weight of the dosage forms described herein, without the capsule shell, may range from about 800 mg to about 850 mg, from about 800 mg to about 900 mg, from about 800 mg to about 950 mg, from about 800 mg to about 1000 mg, from about 800 mg to about 1050 mg, from about 800 mg to about 1100 mg, from about 800 mg, to about 1150 mg, from about 800 mg to about 1200 mg, from about 850 mg to about 900 mg, from about 850 mg to about 950 mg, from about 850 mg to about 1000 mg, from about 850 mg to about 1050 mg, from about 850 mg to about 1100 mg, from about 850 mg to about 1150 mg, from about 850 mg to about 1200 mg, from about 900 mg to about 950 mg, from about 900 mg to about 1000 mg, from about 900 mg to about 1050 mg, from about 900 mg to about 1100 mg, from about 900 mg to about 1150 mg, from about 900 mg to about 1200 mg, from about 950 mg to about 1000 mg, from about 950 mg to about 1050 mg, from about 950 mg to about 1100 mg, from about 950 mg to about 1150 mg, from about 950 mg to about 1200 mg, from about 1000 mg to about 1050 mg, from about 1000 mg to about 1100 mg, from about 1000 mg to about 1150 mg, from about 1000 mg to about 1200 mg, from about 1050 mg to about 1100 mg, from about 1050 mg to about 1150 mg, from about 1050 mg to about 1200 mg, from about 1100 mg to about 1150 mg, from about 1100 mg to about 1200 mg, or from about 1150 mg to about 1200 mg Also, the inventors contemplate that the dosage forms used to deliver an effective amount of the compositions of the present invention may be divided or delivered between two, three, four, or five, etc., dosage forms such as tablets at each oral dosing.

Use of the present invention might allow for a reduction in the use of conventional statins such that side effects will be significantly reduced or avoided. Use of the present invention may allow people on conventional statins to reduce their effective dosages.

The following machinery and equipment may be used to make the compositions of the present invention: a stainless steel mixer, a capsule-filling machine or tableting machine, a filming machine, auxiliary equipment, electromagnets for induction sealing, a machine for heat shrink film, and an inkjet printer.

Basic and additional raw materials contemplated for use with the present invention include raw materials produced in regulated plants subject to all technological and hygienic standards and requirements, accompanied by documents of origin and suitability.

In one preferred embodiment, a dosage form of the present invention comprises, consists essentially of, or consists of, policosanol in the amount of about 10 mg, dry yeast extract of red rice in the amount of about 330 mg, dry extract of *Lespedeza capitata* in the amount of about 240 mg, dry grape seed extract in the amount of about 120 mg, and a hydroxypropylmethylcellulose capsule weighing about 163 mg, for a total capsule weight of about 860 mg. In an alternative embodiment, a dosage form of the present invention comprises, consists essentially of, or consists of, policosanol in the amount of about 10 mg, dry yeast extract of red rice in the amount of about 700 mg, dry extract of *Lespedeza capitata* in the amount of about 240 mg, dry grape seed extract in the amount of about 120 mg, and a hydroxypropylmethylcellulose capsule weighing about 163 mg, for a total capsule weight of about 1230 mg. As noted above, it is contemplated by the inventors that payload delivery of the active ingredients may be accomplished using only one dosage form per administration, or by using multiple dosage forms wherein the payload of active ingredients is divided between the multiple dosage forms. For example, in another alternative embodiment, active ingredients comprising about 10 mg of policosanol, about 700 mg of dry yeast extract of red rice, about 240 mg of dry extract of *Lespedeza capitata*, and about 120 mg of dry grape seed extract are divided between two hydroxypropylmethylcellulose capsules, such that each capsule contains about 535 mg of active ingredients.

In a preferred embodiment, the manufacturing process of the product includes the following phases: (1) weighing active substances according to the one-tablet rate; (2) mixing and homogenization of the active substances in a stainless steel mixer; (3) dosing and dispensing of the product into capsules via a capsule-filling machine; (4) sorting and separation of technological waste after performing item 3 of the technological process—maximum allowed up to 10%—as a result of spills, dusting, adjustments and defects during operation; (5) counting and filling in bottles; (6) placing a thermo shrink film; and (7) printing the markings by using an inkjet printer.

In one embodiment, a dosage form of the present invention comprises, consists essentially of, or consists of, policosanol in the amount of about 10 mg, dry yeast extract of red rice in the amount of about 700 mg, dry extract of *Lespedeza capitata* in the amount of about 240 mg, dry grape seed extract in the amount of about 120 mg, microcrystalline cellulose in the amount of about 80 mg, polyvinylpyrrolidone in the amount of about 150 mg, magnesium stearate in the amount of about 10 mg, talc in the amount of about 10 mg, and film coating in the amount of about 40 mg, for a total tablet weight of about 1360 mg. As noted above, it is contemplated by the inventors that payload delivery of the active ingredients may be accomplished using only one dosage form per administration, or by using multiple dosage forms wherein the payload of active ingredients is divided between the multiple dosage forms.

In one embodiment, the manufacturing process of the product includes the following phases: (1) weighing excipients and active substances according to the one-tablet rate; (2) mixing of the excipients with the active substances and homogenization in a stainless steel mixer; (3) granulation by (a) humidification of the mixed active substance by water-alcohol solution, (b) drying at temperatures up to 40° C., (c) sieving the dried mixture, and (d) input of excipients in the active mixture; (4) dosing and tableting of the product via a tablet machine; (5) filming of the tablets by means of a filming machine (30 to 40% technological loss due to the volatility of the material); (6) sorting and separation of technological waste after performing items 4 and 5 of the technological process—maximum allowed up to 10%—as a result of spills, dusting, adjustments and defects during operation; (7) counting and filling in bottles; (8) placing a thermo shrink film; and (9) printing the markings by using an inkjet printer In a preferred embodiment, an initial dosage may be two capsules or tablets per day, taken once about 10-20 minutes after dinner. In an alternative embodiment, the dosage may be one capsule or tablet per day, taken about 10-20 minutes after dinner. In another alternative embodiment, the daily intake is one or two capsules or tablets before meals. The one time daily dosage taken in the evening may be more effective compared to being taken in the morning due to the fact that cholesterol is synthesized mainly during the night. The dosage of 2 (two) capsules or tablets in the evening is contemplated in the cases when the levels of the total plasma cholesterol is equal to or more than 6.4 mmol/l. In the cases of levels lower than 6.4 mmol/l of the total cholesterol, 1 (one) capsule or tablet is contemplated in the evening along with adherence to a cholesterol reducing diet.

It is also contemplated that the daily dosage may be divided and taken at two or more different times during the day. For example, the daily dosage may be divided into two parts, with one part taken in the morning and one part taken in the evening. The daily dosage may be divided into two, three, four, five, or more parts, which may be taken at different times of day, before or after meals, or at various designated times.

It is also contemplated that the dosage of compositions of the present invention should be reduced, in case the concentration of the plasma LDL cholesterol becomes less than 1.9 mmol/l (75 mg/dl) or if the concentration of the total cholesterol in the plasma becomes less than 3.6 mmol/l (140 mg/dl).

In some of the cases with patients suffering from family homozygous hypercholesterolemia, it is contemplated that the compositions of the present invention would have moderately weaker effect, probably due to the lack of LDL receptors. In the case of such patients it may be possible to observe slight increase of the serum transaminases.

It is also contemplated that compositions of the present invention may moderately reduce triglycerides and shows moderate results in patients in whom hypertrigylceridemia is the major anomaly.

The present inventors also contemplate that it is recommended to apply a standard cholesterol-reducing diet both before and during the therapy with compositions of the present invention. In any event, the maximum recommended daily dosage contemplated by the present inventors is 3 (three) capsules or tablets, assuming that each capsule or tablet is delivered in a format that delivers policosanol in the amount of 10 mg, dry yeast extract of red rice in the amount of 700 mg, dry extract of Lespedeza capitata in the amount of 240 mg, and dry grape seed extract in the amount of 120 mg.

The present inventors also contemplate that, if it is necessary to change the dosage of the compositions of the present invention, that this should not be done at an interval shorter than four weeks.

As an accompanying therapy, compositions of the present invention may be effective taken independently or in a combination of products dissolving the bile acids. Also, it is contemplated that it would not be necessary to change the dosage in subjects with moderate level of kidney insufficiency due to the fact that the inhibitors of HMG-CoA reductase in the preparation are not subjected to considerable renal secretion. Due to the presence of lespecapitoside (C-glycoside from the group of bioflavonoids) in the present inventive compositions, which is one of the main active components in the extract from Lespedeza capitata, the preparation is contemplated for use by subjects suffering from chronic and acute kidney diseases (CKD and AKD). The safety and efficiency of the application of compositions of the present invention in, for example, children under 18 years has not studied and, therefore, the present inventive compositions are not recommended for persons under 18 years. The present inventors contemplate that the elderly patients may also enjoy the benefits of the present inventive compositions.

The efficacy and safety of present inventive compositions and associated methods are based on the selection of natural components: policosanol, which is highly effective in lowering LDL and increasing HDL cholesterol; mevinolinic acid, which directly inhibits 3-hydroxy-3-methyl-glutaryl-coenzyme A reductase (HMG-CoA reductase) in the liver, kaempferol 3,7-dirhamnoside (in Lespedeza capitata) with proven anti-atherosclerotic action by modulation of gene expression of protein, and gallic acid, catechin, and epicatechin (in grape seed extract), which are pancreatic cholesterol esterase inhibitors and have the potential to change the cholesterol metabolism in a number of ways. It is believed that cholesterol esterase contributes to the presence of free cholesterol by catalyzing the cholesterol ester hydrolysis and contributes to the formation of lysolecithin-containing micelles which are effective cholesterol absorption agents, catalyzing the lecithin hydrolysis.

Compositions of the present invention contain natural components and derivatives, which in small amounts affect multiple stages of the metabolism of cholesterol at endogenous and exogenous levels. Thus, the inventive preparations allow patients to avoid taking cholesterol-lowering products for prolonged time and to avoid contraindications.

EXAMPLES

Example 1

Clinical trial with compositions similar to those of the present invention, but excluding policosanol, in patients with hyperlipidemia In the nephrology and transplantation clinic of the Alexandrovska University Hospital in Sofia, treatment with compositions comprising dry yeast extract of red rice, dry extract of Lespedeza capitata, and dry grape seed extract along with excipients was performed in patients with hyperlipidemia. Average patient age was 39±9 years following renal creatinine and creatinine clearance. The antihyperlipidemic effect of the compositions of the present invention, its potential hepatotoxic effect, as well as its effect were studied in the different patient groups, i.e., a group treated with the inventive compositions alone, a group switching from statins to the inventive compositions due to hepatotoxicity, a renal transplantation group and a group of non-transplanted patients.

The tested composition was effective in the treatment of hyperlipidemia. The antihyperlipidemic effect of the test composition was comparable to that of statins. The test composition did not have the hepatotoxic effect of statins. The test compositions could be used successfully in different patient groups with different etiology of hyperlipidemia, both as a first drug and in the substitution of statins. The test composition did not have a negative effect on kidney function.

Example 2

Clinical trial with a composition of the present invention in patients with hypercholesterolemia.

The clinical trial was conducted under the guidance of Prof. Emil Dimitrov Paskalev at the Aleksandrovska University Multi-Specialty Hospital in Sofia, Bulgaria.

A formulation comprising policosanol in the amount of 10 mg, dry yeast extract of red rice in the amount of 700 mg, dry extract of Lespedeza capitata in the amount of 240 mg, and dry grape seed extract in the amount of 120 mg per tablet was given at a dose of two tablets per day taken 10-20 minutes after the evening meal, for a period of 90 days.

The study included 30 patients having hypercholesterolemia. Of the total number of patients, 15 were men and 15 were women, with an average age of 62 years and an age range of 55 to 69 years. Patients were monitored for total serum cholesterol, HDL-cholesterol, LDL-cholesterol, triglycerides, enzyme serum creatinine, glomerular filtration, urea, uric acid, glutamate oxalate transaminase (GOT), glutamate pyruvate transaminase (GPT), alkaline phosphatase (AF), gamma glutamyl transpeptidase (GGT), lactate dehydrogenase (LDH), bilirubin, blood glucose, blood pressure, muscle pain, and rhabdomyolysis. Cholesterol, triglyceride, and glomerular filtration (GF) measurements at the beginning of the study, as compared to the normal levels found in healthy individuals, are shown in Table 4.

TABLE 4

| | Patient measurements at beginning of study | Normal measurements |
|---|---|---|
| Average total cholesterol (mmol/l) | 6.3 ± 0.5 | <5.2 |
| Average HDL-cholesterol (mmol/l) | 1.25 ± 0.1 | >1.45 |
| Average LDL-cholesterol (mmol/l) | 3.56 ± 0.32 | <3.0 |
| Average triglycerides (mmol/l) | 2.2 ± 0.35 | <1.7 |
| Average GF (ml/min/1.73m$^2$) | 86 ± 26 | ≥90 |

The change in total cholesterol level is shown in FIG. 1. The reduction in total cholesterol was greater in the first half of the study, but the levels continued to decline until the end of the study, at which time the total cholesterol was at normal levels.

Figure 2:
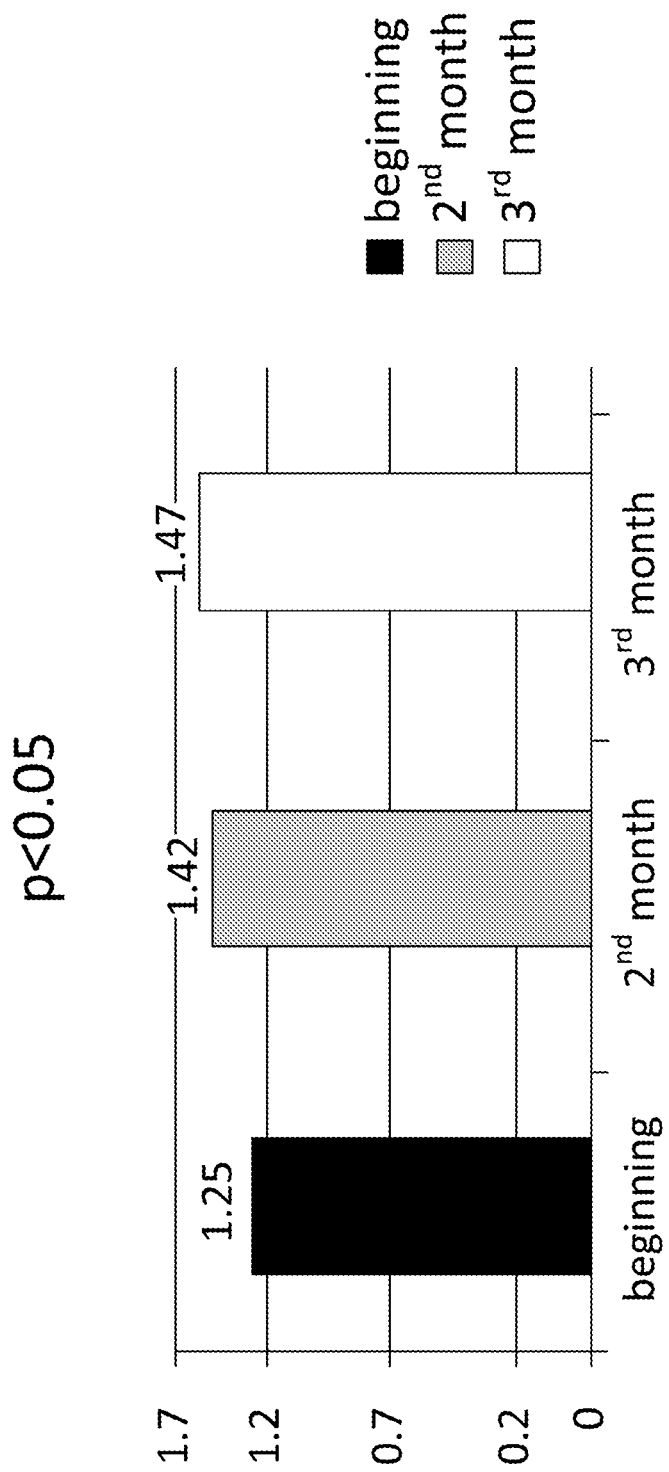
FIG. 2 illustrates the average LDL-cholesterol of the study patients measured at the beginning of the study, after 60 days ("$2^{nd}$ month"), and at the end of the study after 90 days ("$3^{rd}$ month), shown in mmol/l.

The change in HDL-cholesterol is shown in FIG. 2. The levels increased over the course of the study, reaching normal levels by the 90-day measurement.

Figure 3:
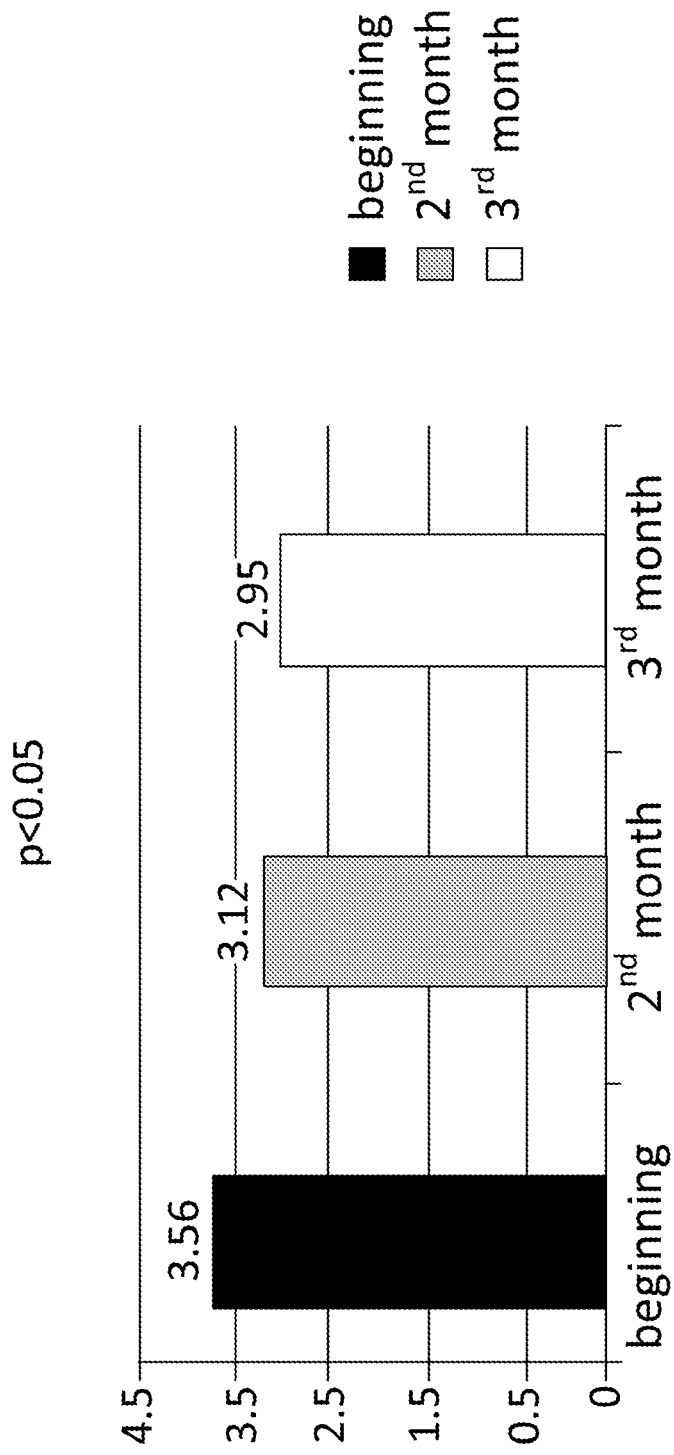
FIG. 3 illustrates the average HDL-cholesterol of the study patients measured at the beginning of the study, after 60 days ("$2^{nd}$ month"), and at the end of the study after 90 days ("$3^{rd}$ month), shown in mmol/l.

The change in LDL-cholesterol is shown in FIG. 3. The levels decreased over the course of the study, also reaching normal levels by the 90-day measurement.

The results showing decreased total cholesterol, increased HDL-cholesterol, and decreased LDL-cholesterol were all calculated to be statistically significant, with $p<0.05$ in each case.

Figure 4:
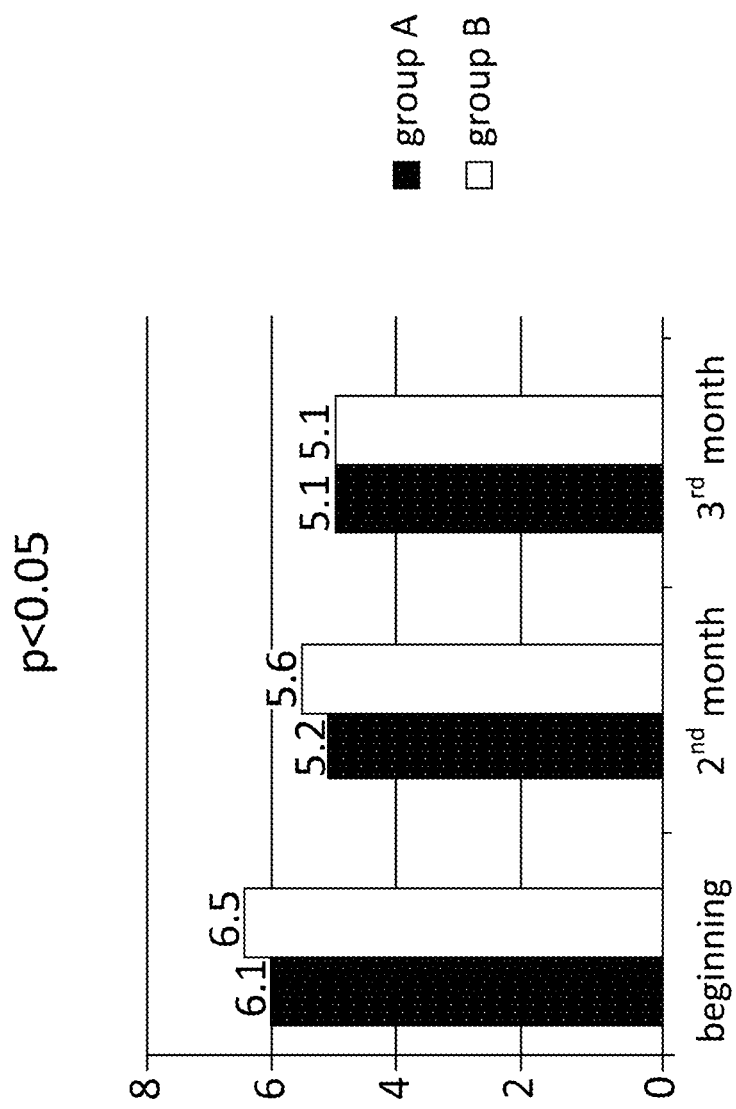
FIG. 4 illustrates the average serum total cholesterol of the study patients measured at the beginning of the study, after 60 days ("$2^{nd}$ month"), and at the end of the study after 90 days ("$3^{rd}$ month), shown in mmol/l, when the patients were divided into two groups based on glomerular filtration (GF). Group A patients were identified as having normal GF at the beginning of the study, while Group B patients were identified as having slightly or moderately reduced GF at the beginning of the study.

The patients were divided into two subgroups according to glomerular filtration (GF) measured at the beginning of the study. Group A consisted of 18 patients with normal GF (≥90 ml/min/1.73 m$^2$) and mean creatinine levels of 89±7 µmol/l. Group B consisted of 12 patients with slightly or moderately reduced GF (76-30 ml/min/1.73 m$^2$) and mean creatinine levels of 182±18 µmol/l. The changes in total cholesterol over the course of the study for each subgroup are shown in FIG. 4. Both subgroups showed a decrease in total cholesterol levels, reaching normal levels by the 90-day measurement. The decrease was calculated to be statistically significant by, with $p<0.05$, and there was no statistical difference between the two groups.

Figure 5:
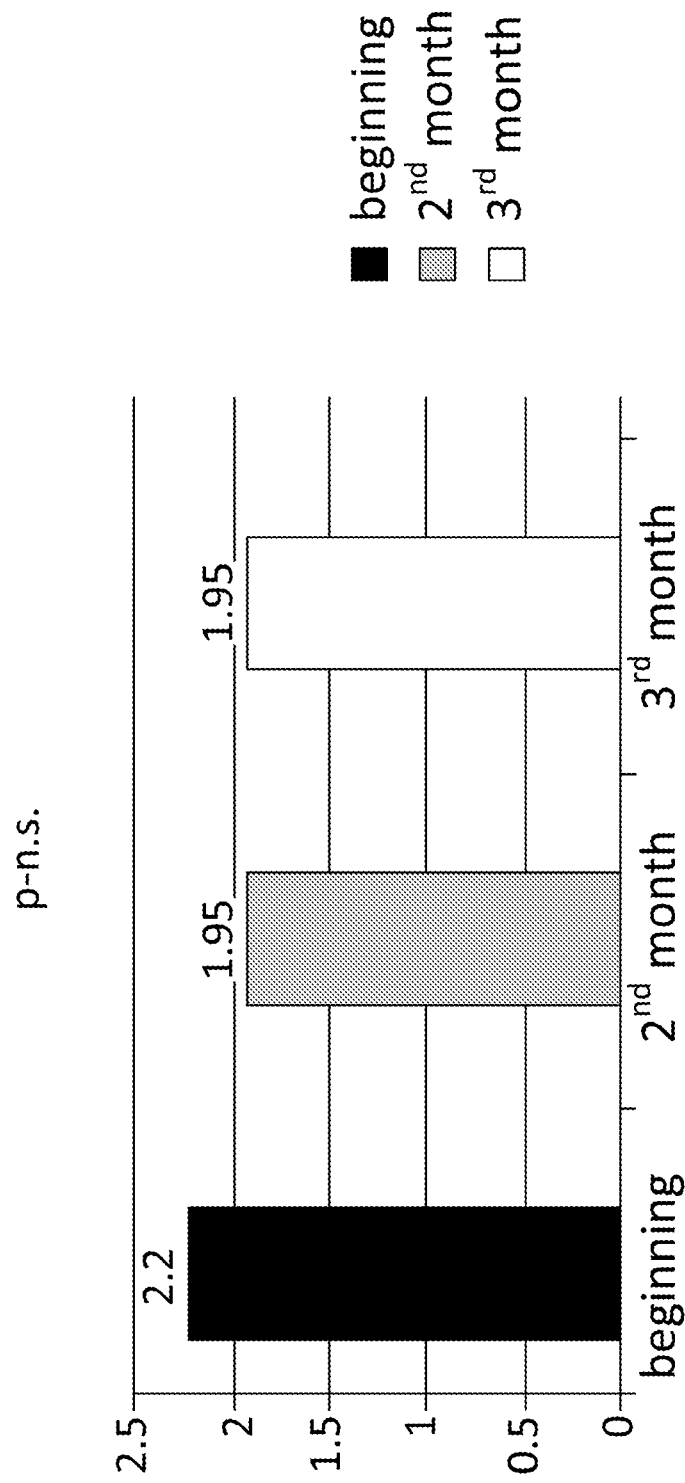
FIG. 5 illustrates the average serum triglyceride of the study patients measured at the beginning of the study, after 60 days ("$2^{nd}$ month"), and at the end of the study after 90 days ("$3^{rd}$ month), shown in mmol/l.

The patients were also monitored for serum triglyceride levels, as shown in FIG. 5. Although the triglyceride levels decreased slightly over the course of the study, the decrease was not statistically significant.

The other parameters being monitored, urea, uric acid, GOT, GPT, AF, GGT, LDH, bilirubin, blood glucose, and blood pressure, showed no significant change over the course of the study.

Patients were also monitored and questioned for side effects such as muscle pain or weakness (a sign of rhabdomyolysis), and gastrointestinal symptoms such as decreased appetite, nausea, stomach upset, and heartburn. No significant incidence of such side effects was identified.

The tested composition was effective in normalizing serum total cholesterol, HDL-cholesterol, and LDL-cholesterol in patients with hypercholesterolemia. The tested composition did not result in any observed negative side effects, nor did it worsen renal function in patients having impaired renal function. Accordingly, the composition provides a safe, effective treatment for patients with hypercholesterolemia.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including, but not limited to, U.S. Provisional Patent Application No. 62/613,714 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An oral delivery capsule dosage form for regulating the level of total blood cholesterol comprising a composition consisting of policosanol, a dry extract of red rice yeast, a dry grape seed extract, and a dry extract of Lespedeza capitata.

2. The dosage form of claim 1, wherein the composition includes policosanol, a dry extract of red rice yeast, a dry grape seed extract, and a dry extract of Lespedeza capitata in amounts effective for disruption or interruption of a metabolic pathway leading to biosynthesis of cholesterol and cholesterol ester.

3. The dosage form of claim 1, wherein the dry extract of red rice yeast includes mevinolinic acid as its primary active component.

4. The dosage form of claim 1, wherein the composition includes the following ratio of active components:
   policosanol from 1% to 2% (w/w);
   dry extract of red rice yeast from 60% to 70% (w/w);
   dry grape seed extract from 8% to 15% (w/w); and
   dry extract of Lespedeza capitata from 17% to 27% (w/w).

5. The dosage form of claim 1, wherein the composition includes the following amounts of active components:
   about 10 mg policosanol;
   about 700 mg dry extract of red rice yeast;
   about 120 mg dry grape seed extract; and
   about 240 mg dry extract of Lespedeza capitata.

6. The dosage form of claim 1, wherein the composition includes the following amounts of active components:
   about 10 mg policosanol;
   about 330 mg dry extract of red rice yeast;
   about 120 mg dry grape seed extract; and
   about 240 mg dry extract of Lespedeza capitata.

7. The dosage form of claim 1, wherein the capsule comprises one or more excipients selected from the group consisting of hydroxypropyl methylcellulose, pullulan, gelatin, starch from vegetable sources, and cellulose.

8. The dosage form of claim 7, wherein the starch is starch from cassava root.

9. The dosage form of claim 7, wherein the capsule dosage form excipient is hydroxypropyl methylcellulose.

10. The dosage form of claim 1, wherein the dry extract of Lespedeza capitata is from the stem and leaf of the plant.

11. The dosage form of claim 1, wherein the policosanol is a natural mixture of aliphatic primary alcohols isolated from purified sugar cane wax of Saccharum officinarum L.

12. The dosage form of claim 11, wherein the policosanol comprises octacosanol in an amount greater than or equal to 50%.

13. The dosage form of claim 11, wherein the policosanol comprises about 51.54% octacosanol, about 24.43% triacontanol, and about 15.80% hexacosanol.

14. The dosage form of claim 1, wherein the composition consists of the following amounts of active components: about 10 mg policosanol; about 330 mg dry extract of red rice yeast; about 120 mg dry grape seed extract; and about 240 mg dry extract of *Lespedeza capitata*, wherein the capsule comprises hydroxypropylmethylcellulose, and wherein the total weight of the capsule and the composition is about 860 mg.

* * * * *